United States Patent
Zeppezauer et al.

(10) Patent No.: US 6,369,203 B1
(45) Date of Patent: *Apr. 9, 2002

(54) PEPTIDES FOR THE PRODUCTION OF PREPARATIONS FOR THE DIAGNOSIS AND THERAPY OF SYSTEMIC LUPUS

(75) Inventors: Michael Zeppezauer, Scheidt; Arno Schönberger, Hamburg, both of (DE); Ladislav Cebecauer, Piešťany (CS)

(73) Assignee: Symbiotec Gesellschaft zur Erforschung und Entwicklung auf dem Gebiet der Biotechnologic mbH, Herborn (DE)

(*) Notice: Subject to any disclaimer, the term of this patent is extended or adjusted under 35 U.S.C. 154(b) by 0 days.

This patent is subject to a terminal disclaimer.

(21) Appl. No.: 07/946,180

(22) Filed: Sep. 16, 1992

(51) Int. Cl.$^7$ ............................................... C07K 16/00
(52) U.S. Cl. ............................... 530/387.2; 530/388.25
(58) Field of Search .................. 424/85.8, 88; 435/69.6, 435/70.2, 70.21, 240.26, 240.27, 965; 530/388.25, 387.2

(56) References Cited

U.S. PATENT DOCUMENTS

| | | | | |
|---|---|---|---|---|
| 2,741,653 A | * | 4/1956 | Kutsky et al. | |
| 3,065,141 A | * | 11/1962 | Gessler et al. | |
| 4,536,479 A | * | 8/1985 | Vander-Mallies | 436/537 |
| 4,699,880 A | * | 10/1987 | Goldstein et al. | 435/172.2 |
| 4,701,442 A | * | 10/1987 | Revici et al. | 514/21 |
| 4,818,763 A | * | 4/1989 | Rusch et al. | 514/2 |
| 5,034,316 A | * | 7/1991 | Weisbart et al. | 435/7.24 |
| 5,182,257 A | * | 1/1993 | Zeppezauer et al. | 514/2 |

FOREIGN PATENT DOCUMENTS

WO 9012806 * 11/1990

OTHER PUBLICATIONS

Laskov et al "Monoclonal antibodies to histones from autoimmune NZB/NZW mice" Eur. J. Immunol. vol. 14, No. 1, p. 74–81, 1984.*

Genomics, BD. 10, Nr. 4, Aug. 1991, Seiten (pps.) 940–948, Albig et al., "Isolation and Characterization of two human H1 histone genes . . . Genes".

J. Biochem., Bd. 85, Nr. 2, 1979, pp. 615–624, Ohe et al., "Human spleen histone H2B, isolation and aminoacid sequence".

Int. Arch. Allergy Appl. Immunol., Bd. 89, Nr. 2–3, 1989, pp. 288–296, Muller et al., "Reactivity of autoantibodies in systemic lupus . . . peptides".

J. Immunology, Bd. 144, Nr. 12, June 15, 1990, pp. 4633–4640, Portanova et al., Histone autoantigens in murine lupus : definition of a major epitope . . . Chromatin.

Mol. Immnuol., Bd. 26, Nr. 8, Aug., 1989, pp. 749–758, Monestier, "Monoclonal anti–histone H1 autoantibodies from MRL lpr/lpr mice".

Autoimmunity, Bd. 9, Nr. 1, 1991, pp. 13–19, Minota et al., "Specificity of autoantibodies to histone H1 in SLE : relationship to DNA–binding domains".

Arthritis Rheum., Bd. 33, Nr. 9SUP, 1990, pp. S51, Minota, "Autoantibody epitope and DNA–binding site on histone H1".

Proc. Natl. Acad. Sci., Bd. 80, Nr. 24, Dec. 1983, pp. 7410–7414, Hardin et al., "Antibodies to histones in systemic lupus, erythematosus: . . . H2B".

J. Mol. Evol., Bd. 25, Nr. 4, 1987, pp. 361–370, Toenjes et al., "A highly conserved sequence in H1 histone genes as an oligonucleotide . . . gene".

Mol. Immunol., Bd. 24, Nr. 3, May 1987, pp. 275–285, Gohill et al., "Antibodies in procainamide–induced and systeic lupus . . . (H1)".

J. Immunology, Bd. 133, Nr. 5, Nov. 1984, pp. 2554–2559, Kotzin et al., "Monoclonal anti–histone autoantibodies derived from murine models of lupus".

Clin. Exp. Immunol., Bd. 86, Nr. 1, Oct. 1991, pp. 124–133, Antanassov et al., "New Zealand white rabbits immunized with RNA–complexed . . . response".

Muller et al, Bioch. et. Bioph. Acta 827:235–246 (1985) "Antigenic Structure of Histone H2B".*

Bond et al, *Monoclonal & Anti–Id: Ab: Probes for Receptor Struct. & Func*, "Anti–Id Ab & Internal Images", pp 141–149 (1984, Alan R Liss Inc.*

Gohill et al, J. of Chromatography, 502: 47–57 (1990) "Purification of Histone H1 Polypeptides by HPLC".*

Portanova et al, J of Immunology, 144:4633–4640 (1990) "Histone Autoantigens in Murine Lupus: Def of Major Epit . . . ".*

Gaulten et al, Ann. Rev. Imm., 4: 253–280, (1986) "Idiotypic Mimicry of Biological Receptors".*

* cited by examiner

*Primary Examiner*—Sheela Huff
(74) *Attorney, Agent, or Firm*—Eugene C. Raucidlo; Greenburg Traurig, LLP

(57) ABSTRACT

Peptides are proposed with antigenic or immunogenic determinants, which result from autoantibodies in the body fluids of patients, who are suffering from systemic lupus erythematosus (SLE). In the case of the peptides it is preferably a question of the C terminus of H1 with the sequence section 187–211 and the N termini of H2B with the sequence sections 1–35 and 36–76, which are capable of cross reactions with the autoantibodies (anti-histone-antibodies). The invention furthermore provides ways of forming monoclonal antibodies and antiidiotypical antibodies, which are directed against autoantibodies. The diagnosis of SLE is possible in accordance with the invention with a high degree of certainty and the monoclonal antibodies directed against the autoantibodies are suitable for the production of medicaments for the therapy of SLE.

4 Claims, No Drawings

```
                          SEQUENCE LISTING (1) GENERAL INFORMATION:

(iii) NUMBER OF SEQUENCES:    17

(2) INFORMATION FOR SEQ ID NO:1:

(i) SEQUENCE CHARACTERISTICS:
             (A) LENGTH:            25 AMINO ACIDS
             (B) TYPE:              AMINO ACID
             (D) TOPOLOGY:          LINEAR (ii) MOLECULE TYPE:         PEPTIDE (v) FRAGMENT TYPE:         C-terminal (vi) ORIGINAL SOURCE:
             (A) ORGANISM:          CALF
             (F) TISSUE TYPE:       THYMUS (vii) IMMEDIATE SOURCE:      SYNTHETIC (ix) FEATURE:
             (A) NAME/KEY:          Peptide derived from histone H1
             (B) LOCATION:          Location 1 through 25 below
                 represents locations 187-211 in the published sequence.
             (C) IDENTIFICATION METHOD:By experiment (x) PUBLICATION INFORMATION:
             (A) AUTHORS:           COLE, R. David
             (B) TITLE:             Microheterogeneity in H1 histones and
                 its consequences
             (C) JOURNAL:           International Journal of Peptide and
                 Protein Research
             (D) VOLUME:            30
             (F) PAGES:             433 - 449
             (G) DATE:              1987

(xi) SEQUENCE DESCRIPTION: SEQ ID NO: 1:

Lys Pro Lys Ala Ala Lys Pro Lys Ala Ala
                   5                  10

Lys Pro Lys Ala Ala Lys Pro Lys Lys Ala
                  15                  20

Ala Pro Lys Lys Lys
                  25

(2) INFORMATION FOR SEQ ID NO:2:

(i) SEQUENCE CHARACTERISTICS:
             (A) LENGTH:            35 AMINO ACIDS
             (B) TYPE:              AMINO ACID
             (D) TOPOLOGY:          LINEAR
```

-continued

```
    (ii) MOLECULE TYPE:         PEPTIDE (v) FRAGMENT TYPE:         N-terminal fragment (vi) ORIGINAL SOURCE:
         (A) ORGANISM:          CALF
         (F) TISSUE TYPE:       THYMUS (vii) IMMEDIATE SOURCE:      SYNTHETIC (ix) FEATURE:
         (A) NAME/KEY:          N-terminal peptide 1-35 of histone
             H2B
         (C) IDENTIFICATION METHOD:By experiment (x) PUBLICATION INFORMATION:
         (A) AUTHORS:           IWAI, K; et al;
         (B) TITLE:
         (C) JOURNAL:           J.Biochem.
         (D) VOLUME:            72
         (F) PAGES:             357-367
         (G) DATE:              1972

(xi) SEQUENCE DESCRIPTION: SEQ ID NO: 2:

Pro Glu Pro Ala Lys Ser Ala Pro Ala Pro
                5                   10

Lys Lys Gly Ser Lys Lys Ala Val Thr Lys
               15                   20

Ala Gln Lys Lys Asp Gly Lys Lys Arg Lys
               25                   30

Arg Ser Glu Lys Glu
               35

(2) INFORMATION FOR SEQ ID NO:3:

(i) SEQUENCE CHARACTERISTICS:
         (A) LENGTH:            41 AMINO ACIDS
         (B) TYPE:              AMINO ACID
         (D) TOPOLOGY:          LINEAR (ii) MOLECULE TYPE:         PEPTIDE (v) FRAGMENT TYPE:         internal fragment (vi) ORIGINAL SOURCE:
         (A) ORGANISM:          CALF
         (F) TISSUE TYPE:       THYMUS (vii) IMMEDIATE SOURCE:      SYNTHETIC (ix) FEATURE:
         (A) NAME/KEY:          Peptide 36-76 derived from histone
             H2B
         (B) LOCATION:          Location 1 through 41 below
             represents locations 36-76 in the published sequence
         (C) IDENTIFICATION METHOD:By experiment (x) PUBLICATION INFORMATION:
         (A) AUTHORS:           IWAI, K; et al;
         (B) TITLE:
         (C) JOURNAL:           J.Biochem.
         (D) VOLUME:            72
         (F) PAGES:             357-367
         (G) DATE:              1972

(xi) SEQUENCE DESCRIPTION: SEQ ID NO: 3:

Ser Tyr Ser Val Tyr Val Tyr Lys Val Leu
                5                   10

Lys Gln Val His Pro Asp Thr Gly Ile Ser
               15                   20

Ser Lys Ala Met Gly Ile Met Asn Ser Phe
```

```
                         25                  30
Val Asn Asp Ile Phe Glu Arg Ile Ala Gly
                                 35                  40

Glu
 41

(2) INFORMATION FOR SEQ ID NO:4:

(i) SEQUENCE CHARACTERISTICS:
        (A) LENGTH:             27 AMINO ACIDS
        (B) TYPE:               AMINO ACID
        (D) TOPOLOGY:           LINEAR (ii) MOLECULE TYPE:         PEPTIDE (v) FRAGMENT TYPE:          N-terminal fragment (vi) ORIGINAL SOURCE:
        (A) ORGANISM:           CALF
        (F) TISSUE TYPE:        THYMUS (vii) IMMEDIATE SOURCE:     SYNTHETIC (ix) FEATURE:
        (A) NAME/KEY:           N-terminal fragment 3-29 derived from
            histone H1
        (B) LOCATION:           Location 1 through 27 below
            represents locations 3-29 in the published sequence.
        (C) IDENTIFICATION METHOD:By experiment (x) PUBLICATION INFORMATION:
        (A) AUTHORS:            COLE, R. David
        (B) TITLE:              Microheterogeneity in H1 histones and
            its consequences
        (C) JOURNAL:            International Journal of Peptide and
            Protein Research
        (D) VOLUME:             30
        (F) PAGES:              433 - 449
        (G) DATE:               1987

(xi) SEQUENCE DESCRIPTION: SEQ ID NO: 4:

Ala Pro Ala Ala Pro Ala Ala Ala Pro Pro
                 5                  10

Ala Glu Lys Thr Pro Val Lys Lys Lys Ala
                 15                  20

Ala Lys Lys Pro Ala Gly Ala
                 25      27

(2) INFORMATION FOR SEQ ID NO:5:

(i) SEQUENCE CHARACTERISTICS:
        (A) LENGTH:             21 AMINO ACIDS
        (B) TYPE:               AMINO ACID
        (D) TOPOLOGY:           LINEAR (ii) MOLECULE TYPE:         PEPTIDE (v) FRAGMENT TYPE:          internal fragment (vi) ORIGINAL SOURCE:
        (A) ORGANISM:           CALF
        (F) TISSUE TYPE:        THYMUS (vii) IMMEDIATE SOURCE:     SYNTHETIC (ix) FEATURE:
        (A) NAME/KEY:           Peptide fragment 55-75 derived from
            histone H1
        (B) LOCATION:           Location 1 through 21 below
            represents locations 55-75 in the published sequence.
        (C) IDENTIFICATION METHOD:By experiment
```

```
        (x) PUBLICATION INFORMATION:
            (A) AUTHORS:            COLE, R. David
            (B) TITLE:              Microheterogeneity in H1 histones and
                its consequences
            (C) JOURNAL:            International Journal of Peptide and
                Protein Research
            (D) VOLUME:             30
            (F) PAGES:              433 - 449
            (G) DATE:               1987

(xi) SEQUENCE DESCRIPTION: SEQ ID NO: 5:

Arg Ser Gly Val Ser Leu Ala Ala Leu Lys
                 5                    10

Lys Ala Leu Ala Ala Ala Gly Tyr Asp Val
                15                    20

Glu
 21

(2) INFORMATION FOR SEQ ID NO:6:

(i) SEQUENCE CHARACTERISTICS:
            (A) LENGTH:             20 AMINO ACIDS
            (B) TYPE:               AMINO ACID
            (D) TOPOLOGY:           LINEAR (ii) MOLECULE TYPE:          PEPTIDE (v) FRAGMENT TYPE:          internal fragment (vi) ORIGINAL SOURCE:
            (A) ORGANISM:           CALF
            (F) TISSUE TYPE:        THYMUS (vii) IMMEDIATE SOURCE:       SYNTHETIC (ix) FEATURE:
            (A) NAME/KEY:           Peptide fragment 97-116 derived from
                histone H1
            (B) LOCATION:           Location 1 through 20 below
                represents locations 97-116 in the published sequence.
            (C) IDENTIFICATION METHOD:By experiment (x) PUBLICATION INFORMATION:
            (A) AUTHORS:            COLE, R. David
            (B) TITLE:              Microheterogeneity in H1 histones and
                its consequences
            (C) JOURNAL:            International Journal of Peptide and
                Protein Research
            (D) VOLUME:             30
            (F) PAGES:              433 - 449
            (G) DATE:               1987

(xi) SEQUENCE DESCRIPTION: SEQ ID NO: 6:

Thr Lys Gly Thr Gly Ala Ser Gly Ser Phe
                 5                    10

Lys Leu Asn Lys Lys Ala Ala Ser Gly Glu
                15                    20

(2) INFORMATION FOR SEQ ID NO:7:

(i) SEQUENCE CHARACTERISTICS:
            (A) LENGTH:             41 AMINO ACIDS
            (B) TYPE:               AMINO ACID
            (D) TOPOLOGY:           LINEAR (ii) MOLECULE TYPE:          PEPTIDE (v) FRAGMENT TYPE:          internal fragment (vi) ORIGINAL SOURCE:
            (A) ORGANISM:           CALF
            (F) TISSUE TYPE:        THYMUS
```

```
      (vii) IMMEDIATE SOURCE:         SYNTHETIC (ix) FEATURE:
            (A) NAME/KEY:             Peptide fragment 76-116 derived from
                histone H1
            (B) LOCATION:             Location 1 through 41 below
                represents locations 76-116 in the published sequence.
            (C) IDENTIFICATION METHOD:By experiment (x) PUBLICATION INFORMATION:
            (A) AUTHORS:              COLE, R. David
            (B) TITLE:                Microheterogeneity in H1 histones and
                its consequences
            (C) JOURNAL:              International Journal of Peptide and
                Protein Research
            (D) VOLUME:               30
            (F) PAGES:                433 - 449
            (G) DATE:                 1987

(xi) SEQUENCE DESCRIPTION: SEQ ID NO: 7:

Lys Asn Asn Ser Arg Ile Lys Leu Gly Leu
                 5                  10

Lys Ser Leu Val Ser Lys Gly Thr Leu Val
                15                  20

Glu Thr Lys Gly Thr Gly Ala Ser Gly Ser
                25                  30

Phe Lys Leu Asn Lys Lys Ala Ala Ser Gly
                35                  40

Glu
 41

(2) INFORMATION FOR SEQ ID NO:8:

(i) SEQUENCE CHARACTERISTICS:
            (A) LENGTH:               51 AMINO ACIDS
            (B) TYPE:                 AMINO ACID
            (D) TOPOLOGY:             LINEAR (ii) MOLECULE TYPE:            PEPTIDE (v) FRAGMENT TYPE:            internal fragment (vi) ORIGINAL SOURCE:
            (A) ORGANISM:             CALF
            (F) TISSUE TYPE:          THYMUS (vii) IMMEDIATE SOURCE:         SYNTHETIC (ix) FEATURE:
            (A) NAME/KEY:             Peptide fragment 66-116 derived from
                histone H1
            (B) LOCATION:             Location 1 through 51 below
                represents locations 66-116 in the published sequence.
            (C) IDENTIFICATION METHOD:By experiment (x) PUBLICATION INFORMATION:
            (A) AUTHORS:              COLE, R. David
            (B) TITLE:                Microheterogeneity in H1 histones and
                its consequences
            (C) JOURNAL:              International Journal of Peptide and
                Protein Research
            (D) VOLUME:               30
            (F) PAGES:                433 - 449
            (G) DATE:                 1987

(xi) SEQUENCE DESCRIPTION: SEQ ID NO: 8:

Ala Leu Ala Ala Ala Gly Tyr Asp Val Glu
                 5                  10

Lys Asn Asn Ser Arg Ile Lys Leu Gly Leu
                15                  20
```

```
Lys Ser Leu Val Ser Lys Gly Thr Leu Val
                25                  30

Glu Thr Lys Gly Thr Gly Ala Ser Gly Ser
                35                  40

Phe Lys Leu Asn Lys Lys Ala Ala Ser Gly
                45                  50

Glu
 51

(2) INFORMATION FOR SEQ ID NO:9:

(i) SEQUENCE CHARACTERISTICS:
        (A) LENGTH:             62 AMINO ACIDS
        (B) TYPE:               AMINO ACID
        (D) TOPOLOGY:           LINEAR (ii) MOLECULE TYPE:          PEPTIDE (v) FRAGMENT TYPE:          internal fragment (vi) ORIGINAL SOURCE:
        (A) ORGANISM:           CALF
        (F) TISSUE TYPE:        THYMUS (vii) IMMEDIATE SOURCE:       SYNTHETIC (ix) FEATURE:
        (A) NAME/KEY:           Peptide fragment 55-116 derived from
            histone H1
        (B) LOCATION:           Location 1 through 62 below
            represents locations 55-116 in the published sequence.
        (C) IDENTIFICATION METHOD:By experiment (x) PUBLICATION INFORMATION:
        (A) AUTHORS:            COLE, R. David
        (B) TITLE:              Microheterogeneity in H1 histones and
            its consequences
        (C) JOURNAL:            International Journal of Peptide and
            Protein Research
        (D) VOLUME:             30
        (F) PAGES:              433 - 449
        (G) DATE:               1987

(xi) SEQUENCE DESCRIPTION: SEQ ID NO: 9:

Arg Ser Gly Val Ser Leu Ala Ala Leu Lys
                 5                  10

Lys Ala Leu Ala Ala Ala Gly Tyr Asp Val
                15                  20

Glu Lys Asn Asn Ser Arg Ile Lys Leu Gly
                25                  30

Leu Lys Ser Leu Val Ser Lys Gly Thr Leu
                35                  40

Val Glu Thr Lys Gly Thr Gly Ala Ser Gly
                45                  50

Ser Phe Lys Leu Asn Lys Lys Ala Ala Ser
                55                  60

Gly Glu
     62

(2) INFORMATION FOR SEQ ID NO:10:

(i) SEQUENCE CHARACTERISTICS:
        (A) LENGTH:             17 AMINO ACIDS
        (B) TYPE:               AMINO ACID
        (D) TOPOLOGY:           LINEAR
```

```
        (ii) MOLECULE TYPE:           PEPTIDE (v) FRAGMENT TYPE:           internal fragment (vi) ORIGINAL SOURCE:
              (A) ORGANISM:           CALF
              (F) TISSUE TYPE:        THYMUS (vii) IMMEDIATE SOURCE:        SYNTHETIC (ix) FEATURE:
              (A) NAME/KEY:           Peptide fragment 77-93 derived from
                   histone H2B
              (B) LOCATION:           Location 1 through 17 below
                   represents locations 77-93 in the published sequence.
              (C) IDENTIFICATION METHOD:By experiment (x) PUBLICATION INFORMATION:
              (A) AUTHORS:            IWAI, K; et al;
              (B) TITLE:
              (C) JOURNAL:            J.Biochem.
              (D) VOLUME:             72
              (F) PAGES:              357-367
              (G) DATE:               1972

(xi) SEQUENCE DESCRIPTION: SEQ ID NO: 10:

Ala Ser Arg Leu Ala His Tyr Asn Lys Arg
                5                  10

Ser Thr Ile Thr Ser Arg Glu
            15     17

(2) INFORMATION FOR SEQ ID NO:11:

(i) SEQUENCE CHARACTERISTICS:
              (A) LENGTH:             12 AMINO ACIDS
              (B) TYPE:               AMINO ACID
              (D) TOPOLOGY:           LINEAR (ii) MOLECULE TYPE:           PEPTIDE (v) FRAGMENT TYPE:           C-terminal fragment (vi) ORIGINAL SOURCE:
              (A) ORGANISM:           CALF
              (F) TISSUE TYPE:        THYMUS (vii) IMMEDIATE SOURCE:        SYNTHETIC (ix) FEATURE:
              (A) NAME/KEY:           Peptide fragment 94-105 derived from
                   histone H2B
              (B) LOCATION:           Location 1 through 12 below
                   represents locations 94-105 in the published sequence.
              (C) IDENTIFICATION METHOD:By experiment (x) PUBLICATION INFORMATION:
              (A) AUTHORS:            IWAI, K; et al;
              (B) TITLE:
              (C) JOURNAL:            J.Biochem.
              (D) VOLUME:             72
              (F) PAGES:              357-367
              (G) DATE:               1972

(xi) SEQUENCE DESCRIPTION: SEQ ID NO: 11:

Ile Gln Thr Ala Val Arg Leu Leu Leu Pro
                5                  10

Gly Glu
    12

(2) INFORMATION FOR SEQ ID NO:12:

(i) SEQUENCE CHARACTERISTICS:
              (A) LENGTH:             8 AMINO ACIDS
```

```
            (B) TYPE:                AMINO ACID
            (D) TOPOLOGY:            LINEAR (ii) MOLECULE TYPE:              PEPTIDE (v) FRAGMENT TYPE:              C-terminal fragment (vi) ORIGINAL SOURCE:
            (A) ORGANISM:            CALF
            (F) TISSUE TYPE:         THYMUS (vii) IMMEDIATE SOURCE:           SYNTHETIC (ix) FEATURE:
            (A) NAME/KEY:            Peptide fragment 106-113 derived from
                histone H2B
            (B) LOCATION:            Location 1 through 8 below
                represents locations 106-113 in the published sequence.
            (C) IDENTIFICATION METHOD:By experiment (x) PUBLICATION INFORMATION:
            (A) AUTHORS:             IWAI, K; et al;
            (B) TITLE:
            (C) JOURNAL:             J.Biochem.
            (D) VOLUME:              72
            (F) PAGES:               357-367
            (G) DATE:                1972

(xi) SEQUENCE DESCRIPTION: SEQ ID NO: 12:

Leu Ala Lys His Ala Val Ser Glu
                5               8

(2) INFORMATION FOR SEQ ID NO:13:

(i) SEQUENCE CHARACTERISTICS:
            (A) LENGTH:              12 AMINO ACIDS
            (B) TYPE:                AMINO ACID
            (D) TOPOLOGY:            LINEAR (ii) MOLECULE TYPE:              PEPTIDE (v) FRAGMENT TYPE:              C-terminal fragment (vi) ORIGINAL SOURCE:
            (A) ORGANISM:            CALF
            (F) TISSUE TYPE:         THYMUS (vii) IMMEDIATE SOURCE:           SYNTHETIC (ix) FEATURE:
            (A) NAME/KEY:            Peptide fragment 114-125 derived from
                histone H2B
            (B) LOCATION:            Location 1 through 12 below
                represents locations 114-125 in the published sequence.
            (C) IDENTIFICATION METHOD:By experiment (x) PUBLICATION INFORMATION:
            (A) AUTHORS:             IWAI, K; et al;
            (B) TITLE:
            (C) JOURNAL:             J.Biochem.
            (D) VOLUME:              72
            (F) PAGES:               357-367
            (G) DATE:                1972

(xi) SEQUENCE DESCRIPTION: SEQ ID NO: 13:

Gly Thr Lys Ala Val Thr Lys Tyr Thr Ser
                5                   10

Ser Lys
    12

(2) INFORMATION FOR SEQ ID NO:14:

(i) SEQUENCE CHARACTERISTICS:
            (A) LENGTH:              21 AMINO ACIDS
```

```
            (B) TYPE:                 AMINO ACID
            (D) TOPOLOGY:             LINEAR (ii) MOLECULE TYPE:             PEPTIDE (v) FRAGMENT TYPE:             N-terminal fragment (vi) ORIGINAL SOURCE:
            (A) ORGANISM:             CALF
            (F) TISSUE TYPE:          THYMUS (vii) IMMEDIATE SOURCE:          SYNTHETIC (ix) FEATURE:
            (A) NAME/KEY:             Peptide fragment 1-21 derived from
                histone H2B
            (C) IDENTIFICATION METHOD:By experiment (x) PUBLICATION INFORMATION:
            (A) AUTHORS:              IWAI, K; et al;
            (B) TITLE:
            (C) JOURNAL:              J.Biochem.
            (D) VOLUME:               72
            (F) PAGES:                357-367
            (G) DATE:                 1972

(xi) SEQUENCE DESCRIPTION: SEQ ID NO: 14:

Pro Glu Pro Ala Lys Ser Ala Pro Ala Pro
                5                  10

Lys Lys Gly Ser Lys Lys Ala Val Thr Lys
               15                  20

Ala
 21

(2) INFORMATION FOR SEQ ID NO:15:

(i) SEQUENCE CHARACTERISTICS:
            (A) LENGTH:               8 AMINO ACIDS
            (B) TYPE:                 AMINO ACID
            (D) TOPOLOGY:             LINEAR (ii) MOLECULE TYPE:             PEPTIDE (v) FRAGMENT TYPE:             N-terminal fragment (vi) ORIGINAL SOURCE:
            (A) ORGANISM:             CALF
            (F) TISSUE TYPE:          THYMUS (vii) IMMEDIATE SOURCE:          SYNTHETIC (ix) FEATURE:
            (A) NAME/KEY:             Peptide fragment 4-11 derived from
                histone H2B
            (B) LOCATION:             Location 1 through 8 below
                represents locations 4-11 in the published sequence.
            (C) IDENTIFICATION METHOD:By experiment (x) PUBLICATION INFORMATION:
            (A) AUTHORS:              IWAI, K; et al;
            (B) TITLE:
            (C) JOURNAL:              J.Biochem.
            (D) VOLUME:               72
            (F) PAGES:                357-367
            (G) DATE:                 1972

(xi) SEQUENCE DESCRIPTION: SEQ ID NO: 15:

Ala Lys Ser Ala Pro Ala Pro Lys
                5           8

(2) INFORMATION FOR SEQ ID NO:16:

(i) SEQUENCE CHARACTERISTICS:
```

```
              (A) LENGTH:              22 AMINO ACIDS
              (B) TYPE:                AMINO ACID
              (D) TOPOLOGY:            LINEAR (ii) MOLECULE TYPE:              PEPTIDE (v) FRAGMENT TYPE:              N-terminal fragment (vi) ORIGINAL SOURCE:
              (A) ORGANISM:            CALF
              (F) TISSUE TYPE:         THYMUS (vii) IMMEDIATE SOURCE:           SYNTHETIC (ix) FEATURE:
              (A) NAME/KEY:            Peptide fragment 1-22 derived from
                  histone H2A
              (C) IDENTIFICATION METHOD:By experiment (x) PUBLICATION INFORMATION:
              (A) AUTHORS:             Sautier et al
              (B) TITLE:
              (C) JOURNAL:             European Journal of Biochemistry
              (D) VOLUME:              41
              (F) PAGES:               563-576
              (G) DATE:                1974

(xi) SEQUENCE DESCRIPTION: SEQ ID NO: 16:

Ser Gly Arg Gly Lys Gln Gly Gly Lys Ala
              5                   10

Arg Ala Lys Ala Lys Thr Arg Ser Ser Arg
             15                   20

Ala Gly
    22

(2) INFORMATION FOR SEQ ID NO:17:

(i) SEQUENCE CHARACTERISTICS:
              (A) LENGTH:              129 AMINO ACIDS
              (B) TYPE:                AMINO ACID
              (D) TOPOLOGY:            LINEAR (ii) MOLECULE TYPE:              PEPTIDE (v) FRAGMENT TYPE:

(vi) ORIGINAL SOURCE:
              (A) ORGANISM:            CALF
              (F) TISSUE TYPE:         THYMUS (vii) IMMEDIATE SOURCE:

(ix) FEATURE:
              (A) NAME/KEY:            Histone H2A (1-129)
              (C) IDENTIFICATION METHOD:By experiment (x) PUBLICATION INFORMATION:
              (A) AUTHORS:             Sautier et al
              (B) TITLE:
              (C) JOURNAL:             European Journal of Biochemistry
              (D) VOLUME:              41
              (F) PAGES:               563-576
              (G) DATE:                1974

(xi) SEQUENCE DESCRIPTION: SEQ ID NO: 17:

Ser Gly Arg Gly Lys Gln Gly Gly Lys Ala
              5                   10

Arg Ala Lys Ala Lys Thr Arg Ser Ser Arg
             15                   20

Ala Gly Leu Gln Phe Pro Val Gly Arg Val
             25                   30
```

```
His Arg Leu Leu Arg Lys Gly Asn Tyr Ala
                35                  40

Glu Arg Val Gly Ala Gly Ala Pro Val Tyr
                45                  50

Leu Ala Ala Val Leu Glu Tyr Leu Thr Ala
                55                  60

Glu Ile Leu Glu Leu Ala Gly Asn Ala Ala
                65                  70

Arg Asp Asn Lys Lys Thr Arg Ile Ile Pro
                75                  80

Arg His Leu Gln Leu Ala Ile Arg Asn Asp
                85                  90

Glu Glu Leu Asn Lys Leu Leu Gly Lys Val
                95                  100

Thr Ile Ala Gln Gly Gly Val Leu Pro Asn
                105                 110

Ile Gln Ala Val Leu Leu Pro Lys Lys Thr
                115                 120

Glu Ser His His Lys Ala Lys Gly Lys
                125             129
```

PEPTIDES FOR THE PRODUCTION OF PREPARATIONS FOR THE DIAGNOSIS AND THERAPY OF SYSTEMIC LUPUS

The present invention relates to peptides with antigenic or immunogenic determinants, which may be recognized by autoantibodies in the body fluids of patients, who are suffering from systemic lupus erythematosus (SLE).

Diseases of the "rheumatic group" are characterized by a large number of clinical phenomena and by a wide spectrum of autoantibodies. The latter are directed against various different components of normal cells. The said diseases include systemic lupus erythematosus (SLE) which may occur spontaneously or may be induced by medicaments. In the case of SLE the occurrence of autoantibodies is particularly frequent, which are directed against components of the cell nucleus (antinuclear antibodies, ANA's), these including inter alia double strand desoxyribonucleic acid (DS-DNA) and histone proteins, ribonucleic acid (RNA), complexes of DNA and histones as well as enzymes. Histones consist of a number of classes of proteins, the so-called core histones H1A, H2B, H3 and H4, which are found in the nucleosomes, and the linker histones H1 and H5, to which linking functions are attributed in the formation of chromatin. Many attempts have been made to correlate the frequency of autoantibodies, which are directed against special antigens, with certain rheumatic syndromes.

It has been discovered that in the case a patient with SLE autoantibodies against histones (AHA's, anti-histone autoantibodies) occur more frequently. Normally the "enzyme linked immuno-sorbent assay" (ELISA) is utilized for determination, in the case of which the sera of patients and of healthy control subjects are tested on purified cell components (i. e. antigens). Pure histone is inter alia employed as an antigen for the testing of SLE sera.

Furthermore additionally synthetic peptides or those produced by the degradation of natural histones are used, which consist of sequence parts of the said histones.

In this respect it has been seen that in the case of use of the individual histones and histone peptides:

(i) the frequency of a positive reaction in an ELISA is not greater than 50% and that
(ii) the frequency of a positive reaction in the case of patient sera related to other rheumatic diseases is large (false positive results).

Thus recently a study concerning the predictive value of recognition of AHA's of SLE patients (by means of the LE cell test, Smeenk et al., Scand. J. Rheumatology. Suppl. 56, 78–92, 1985) came to the following conclusion: although 95% of SLE patients were positive in the LE test, in fact the chances that a patient with a positive LE test has SLE are only 27%.

It would therefore be a valuable contribution if the predictive value of diagnostic tests for SLE could be improved, that is to say if the percentage of true-positive results as related to false positive ones could be increased.

It would furthermore be valuable if monoclonal antibodies and antiidiotypical antibodies could be formed, which are specific in the very same manner as the antibodies of SLE patients and if antiidiotypical antibodies (monoclonal antibodies) could be produced, which are directed against these monoclonal antibodies or, respectively, the autoantibodies of SLE patients.

One object of the invention is to a achieve these aims.

In order to achieve this and/or other objects appearing from the present specification, claims and drawings, in the present invention a peptide with antigenic or immunogenic determinants, which is recognized by autoantibodies, more particularly in the body liquids of a patient suffering from systemic lupus erythematosus (SLE) is characterized essentially in that the amino acid sequences are:

Further advantageous developments and convenient forms of the invention will be gathered from the features of the further claims and the following description.

The following natural and synthetic peptides were tested
By means of ELISA the epitopes of the autoantibodies of 112 rheumatic and SLE sera were charted with H1, H2B and H2A peptides. 80% of the SLE sera and 66% of all sera reacted positively both to the C terminus of H1 and also to the N terminus of H2B. The combination of the two regions is therefore to be regarded as a marker sequence and hence as a distinguishing criterion for SLE patients. Both the structural data concerning these regions as well as the antigenity calculations the homologous epitopes of the patient's own antibodies produced in vivo and in vitro underline the dominant antigenic character of the N terminus of H2B and of the C terminus of H1.

For the ELISA (enzyme linked immuno-sorbent assay) F16 modules of the Nunc Company were utilized with a special highly active surface. Dependent on the purpose of the test either the antibody to be tested (in a direct ELISA or sandwich test) or the antigen (in an indirect ELISA) were bound to the surface of the microtitration plate. The antigens were dissolved with a concentration of 50 $\mu$g/ml in a 0.05 M carbonate buffer, pH 9.7. Antibody solutions, supernatant liquid from cells and urine samples were diluted 1 to 3 in the same buffer and in each case 100 $\mu$l were pipetted onto the microtitration plate. Linking took place for 24 hours at 4° C. After emptying the dishes on the following day reactive groups of the microtitration plate were blocked at 36° C. with 250 $\mu$l of blocking solution per dish. For this different blocking solutions were employed: 0.5% (w/v) gelatine in PBS/azide; 1% (w/v) BSA in PBS/azide; 5% (w/v) BSA in PBS/azide; 10% (v/v) equine serum in PBS/azide. The addition was then made of 100 $\mu$l of cell culture supernatant liquid (primary antibodies) or, respectively, the 1 to 250 diluted sera with incubation for one hour at room temperature in the dark. After rinsing the microtitration plate once with Tween solution (consisting of 0.1% (v/v) Tween 20 and 150 mM NaCl) 100 $\mu$l of conjugate (0.3% (v/v) rabbit anti-(mouse-IgG)IgG-HRP or, respectively, rabbit-anti (human-IgG)IgG-HRP were applied thereto by pipetting and incubated at room temperature for one hour. Unbound antibodies were removed by rinsing five times with Tween solution. After the addition of 100 $\mu$l of McIlvanie buffer (116 mM $Na_2HPO_4+2H_2O$, 42 mM citric acid, pH 5.6, including 1.5 mM of orthophenylenediamine and 0.9 mM of $H_2O_2$), the horseradish peroxidase, coupled with the rabbit or, respectively, ovine antibodies, completed the color reaction in the dark, it being arrested with 100 $\mu$l of 2M $H_2SO_4$. After matching against the blind sample, the extinction of the different dishes was ascertained, photometrically at 490 nm with the aid of a Minireader II and a print out was made of the values obtained.

The 122 SLE sera were tested for autoantibodies in an ELISA which indicated that the N terminal range (1–35) of H2B and the C terminal range (187–211) of H1 represent preferred epitopes of SLE autoantibodies. Furthermore the dilution rate of 1 to 250 was found to be more particularly suitable for detection of a wide spectrum of high and low titer sera in an ELISA. In this respect the inventors turned their main attention to the IgG-autoantibodies.

The results were evaluated as follows: an ELISA on a patient was only rated as positive if both extinctions >0.2

(cut off=0.2 from dummy measurements and correction factor in the case of stray values >0.2) and distinctly higher than the values in comparison with all other peptides.

Of the 122 sera 68% were positive with respect to the peptide combination. The 122 sera were composed of 80 SLE and 42 rheumatic sera. Of the 80 lupus patients 80% were H1-CT and E1 positive, whereas of the 42 rheumatic patients 45% were still H1-CT and E1 positive. Therefore the N terminal ranges of H2B (1–31) and the C terminal range of H1 (187–211) constituted the main antigenic determinants detected of autoantibodies of the lupus patients. The combination of these two peptides may therefore function as a distinguishing criterion for the classification of SLE patients and separating them from rheumatic patients.

In order to produce the monoclonal antibodies (anti-histone-antibodies), which are directed against the autoantibodies in the body liquids of SLE patients, the procedure adopted in the invention was as follows (schedule I):

(1) Analysis of the histone sequences (mathematical model).
(2) Prediction of the antigenic ranges.
(3) Synthesis of peptides in accordance with the antigenic ranges. The peptides are partly produced in a free condition and partly bound on a carrier (TentaGel).
(4a) Immunization of animals (mice) with synthetic peptides in accordance with (3); the peptides must be used bound to a carrier (as for instance on a TentaGel).
(4b) Immunization of spleen cells in vitro with synthetic peptides in accordance with (3). In this case free or carrier-bound peptides may be employed.
(5) Isolation of the spleen cells and fusion with cancer cells to give hybridoma cells; selection of individual (positive) clones.
(6) Isolation of the exuded anti-histone-antibodies (AHA).
(7) Investigation of specificity and activity of the synthetic AHA's using synthetic peptides in accordance with (3) as antigens by means of an ELISA.

In order to produce the antuidiotypical antibodies in accordance with the invention the procedure was as follows in accordance with the invention (schedule II):

(1.1) Selection of the antigen:
    The antigen is for instance an epitope directed against histone peptides H1 (187–211) and H2B(1–35), on the autoantibody in the serum of SLE patients or
(1.2) the corresponding epitope on the monoclonal antibodies, which were produced against this peptide/peptide combination.
(2) Production of the antigen(s).
(2.1) The antibody fraction of the SLE serum is enriched using a conventional method.
(2.2.1) Those autoantibodies are selectively removed from the enriched antibody fraction of the SLE serum by affinity chromatography, which have the epitopes as defined in (1). For this purpose the peptides defined in (1) are bound using suitable methods on suitable carrier materials chemically or adsorptively. As an alternative it is possible as well for the peptides to be synthesized on suitable carrier materials, as for instance TentaGels. It is consequently possible to firstly pass the enriched antibody fraction of the SLE serum through a column with carrier H1 (187–211)-conjugate, to wash it and then to elute the autoantibodies bound on the conjugate using a suitable method. This autoantibody fraction is then passed in a second step through a column with a carrier-H2B (1–35)-conjugate. The double specific or cross specific autoantibodies of interest are then retained and after washing of the column using a suitable method may be eluted. It is furthermore possible to change over the order of affinity steps as well, that is to say firstly to use the carrier-H2B (1–35) and then the carrier-H1C.
(2.2.2) The monoclonal antibodies, which in accordance with (1.2) possess the double specific epitope, are isolated in accordance with schedule I (6) and then purified.

3 Immunization methods
(3.1) In vivo immunization
    The autoantibodies produced in accordance with (2), or monoclonal antibodies are used in the conventional manner for immunization. They may be freely employed in combination with suitable adjuvants or coupled with a suitable carrier, as for instance a Tantagel.
(3.2) In vitro immunization
    The antibodies produced in accordance with (2) may be employed as well in order to immunize spleen cells of suitable experimental animals in vitro using conventional methods.
(4) Isolation of the spleen cells producing antiidiotypical antibodies and fusion with suitable cancer cells to give hybridoma cells.
(5) Selection and culture of individual clones.
(6) Isolation and purification of the monoclonal antuidiotypical antibodies.

It would also be possible not to use step (3) but rather to isolate B-lymphocytes from the blood of SLE patients (or of animals with autoimmune diseases), to fuse them with tumor cells and to isolate those clones from the resulting hybridoma cells which have the specificity noted in (1). The identification of these clones is performed by means of conventional tests, as for instance ELISA, using the peptide/peptide combinations in accordance with the invention.

It is clear that the determination of the concentration of the autoantibodies (anti-histone-antibodies) of SLE patients is not limited to ELISA-type methods.

The AHA concentration may furthermore be determined by radioimmune assay (RIA) using radioactive marked N terminal peptides of H2B and C terminal peptides of H1 or by means of a fluorescence-immuno assay with N terminal peptides, marked to fluoresce, of H2B and C terminal peptides of H1. It will be clear to the man in the art that the detection and ascertainment of concentration for AHA may be performed in other body liquids and components thereof, as for instance urine, besides sera.

It has been found in accordance with the invention that antigenic determinants of the histones H1 and H2 may be characterized both by means of synthetically produced monoclonal antibodies and also by means of human pathogenic autoantibodies. In order to improve the autogenic properties of the very conservative and weakly immunogenic histones, purified classes of histones or selected synthetic peptides are coupled with different carriers.

In vivo immunization with glutaraldehyde cross linked histone complexes lead to an IgM antibody (1/A8/B1) which is directed against conformation antigens. In vivo immunization with histone H1 coupled to Eupergit C led to three further monoclonal IgM antibodies: 1/H4/C3 ($IgG_{2a}$, I/H 4/C6 ($IgG_{2a}$) and 1/H4/C10($IgG_{2a}$), all three having a kappa specificity of the light chain. The epitope of the three monoclonal antibodies was in the C terminus of H1

(187–211). The cross reaction of the antibodies with the T terminus of H2B (22–35) is to be attributed to the sequence and charge homology of the two terminal histone ranges. Two N terminal peptides from H2B, coupled with Eupergit, were employed for in vivo immunization.

As antigens free histones, free peptides and peptides coupled with carriers were used. In vitro immunization with free histone H1 led to an $IgG_{2a}$ antibody with a kappa chain, whose epitope is also the C terminus of H1.

In accordance with the invention it was possible to use TentaGels as a new synthetic carrier material for successful in vitro immunization. TentaGels constitute a new class of grafted copolymeric particles, whose polystyrene nucleus is surrounded by "marginal brush-like" polyoxyethylene tentacles. These carriers may be employed in a "single step method" after peptide synthesis immediately for in vitro immunization. TentaGels are characterized by a very high biocompatibility, chemical inertness, improved hydrophilic properties and last but not least by optimum exposure of uniform haptenic structures for contact with immune-competent cells.

The monoclonal antibodies produced are employed both in different immunological test systems, such as immunodiffusion, hemagglutination, dot blot and various ELISA systems as well as, after coupling with fluorescing isothyocyanate (FITC) and horseradish oxidase (HRP) for the performance of continuous flow cytometry and in the Western blot test.

What is claimed is:

1. Monoclonal antibodies specifically binding both to a peptide having an amino acid sequence as set forth in SEQ. ID. NO. 1, which corresponds to amino acid residues 187–211 at the carboxy-terminus of histone H1, and to a peptide having an amino acid sequence as set forth in SEQ. ID. NO. 2, which corresponds to amino acid residues 1–35 at the amino-terminus of histone H2B.

2. Monoclonal antibodies according to claim 1 wherein the recognized amino acid sequences are modified by peptide bonds selected from the group consisting of:

—CON(CH$_3$)—,
—CH$_2$—CH$_2$—, and
—CO—CH$_2$—.

3. The monoclonal antibodies of claim 1, wherein said monoclonal antibodies exhibits a specifity for said peptides that is similar to that of autoantibodies found in sera of patients suffering from systemic lupus erythematosus (SLE).

4. Antiidiotypic antibodies specifically binding to the monoclonal antibodies of claim 1 and to autoantibodies of SLE patients.

* * * * *